US006925858B2

(12) United States Patent
Miles et al.

(10) Patent No.: US 6,925,858 B2
(45) Date of Patent: Aug. 9, 2005

(54) TURF TEST APPARATUS

(75) Inventors: Erle Miles, Dalton, GA (US); Ken Quarles, Chatsworth, GA (US)

(73) Assignee: Testing Services, Inc., Dalton, GA (US)

( * ) Notice: Subject to any disclaimer, the term of this patent is extended or adjusted under 35 U.S.C. 154(b) by 47 days.

(21) Appl. No.: 10/693,353

(22) Filed: Oct. 23, 2003

(65) Prior Publication Data

US 2005/0087003 A1 Apr. 28, 2005

(51) Int. Cl.⁷ .............................................. G01N 3/00
(52) U.S. Cl. .............................. 73/84; 73/82; 73/12.06
(58) Field of Search ........................... 73/82, 84, 12.04, 73/12.05, 12.06, 12.09, 12.11, 12.13

(56) References Cited

U.S. PATENT DOCUMENTS

| | | | |
|---|---|---|---|
| 3,408,870 A | * 11/1968 | Chumley et al. | 73/865.3 |
| 3,888,108 A | 6/1975 | Brands | |
| 4,359,890 A | * 11/1982 | Coelus | 73/12.13 |
| 4,856,318 A | * 8/1989 | Hogan et al. | 73/12.13 |
| 4,887,459 A | 12/1989 | Thomas | |
| 5,259,240 A | * 11/1993 | Raines et al. | 73/84 |
| 5,390,535 A | 2/1995 | Smock | |
| 5,454,264 A | 10/1995 | Lampinen | |
| 5,471,868 A | 12/1995 | Nolan | |
| 5,490,411 A | * 2/1996 | Hogan | 73/12.13 |
| 5,736,631 A | 4/1998 | Dixon | |
| 6,536,263 B1 | 3/2003 | Wood | |
| 2005/0011249 A1 | * 1/2005 | Mahaffey et al. | 73/12.01 |

* cited by examiner

*Primary Examiner*—Charles Garber
(74) *Attorney, Agent, or Firm*—McNair Law Firm, P.A.

(57) ABSTRACT

A drop test apparatus for determining the resiliency of playing surface comprising a missile for impacting the surface including a guide for providing substantially unrestricted free flight of the missile, a pair accelerometers carried by the missile for producing signals in response to impact with the surface, a converter adapted to receive the accelerometer signals, convert them into computer readable signals and a computer receiving the signals from the converter and producing a graph of the surface hardness.

18 Claims, 5 Drawing Sheets

TURF TEST APPARATUS

BACKGROUND OF THE INVENTION

The instant invention is directed to a testing device which is operative to test the resilience or hardness of an athletic playing surface. In the last decade, artificial playing surfaces for substantially all sports have become the norm. Sports such as football, baseball, tennis, wrestling and others all employ synthetic playing surfaces. It is also important that resiliency of natural playing surfaces fall within selected limits. For purposes such as safety, consistency, effectiveness, etc. it has been deemed beneficial to bring or keep the resiliency or hardness of these surfaces between limits.

As a result a need for testing equipment to insure that playing surfaces fall within selected limits evolved.

There exists testing equipment for the above described purpose such as illustrated by U.S. Pat. No. 5,390,535. The existing equipment does not protect the flight of the dropped missile from interference nor does the result reach a high level of accuracy.

Accordingly, it is an object of this invention to provide surface testing apparatus which is easily set up for testing the surface of an athletic playing area.

Another object of the invention is the provision of surface resilience testing equipment which provides for substantially unrestricted flight of the test missile.

Another object of the invention is a surface resilience testing apparatus which produces a recordable electronic signal.

Another object of the invention is a surface testing apparatus which produces a graph of the surface resilience.

SUMMARY OF THE INVENTION

The instant invention is directed to a drop test apparatus for testing the resilience of playing surfaces. The testing apparatus includes a substantially clear circular guide tube formed of synthetic material having an open interior and first and second open ends. An upper flange is mounted with the second end. The flange is formed with an opening of slightly less diameter than the interior of the tube, allowing access to the tube from the second end. A missile mounted on a centering handle is arranged above the second end. The missile carries a sensing member which is connected with a converting unit. The converting unit is adapted to receive signals from the sensing member and convert these signals into computer readable signals. The apparatus operates by releasing the missile to free fall through the guide tube to impact upon the playing surface causing the sensing member to produce and send a signal to the converting unit which then converts the signals and transmits the converted signal to a receiving and display unit.

The tube is formed of clear plastic and includes elongated vents arranged about and along its periphery. The vents act to vent air from the tube during movement of the missile there through. There are also radially extending grooves arranged about the lower surface of the base. These grooves also act to vent air from the tube during movement of the missile.

The missile includes a bearing comprising synthetic rings arranged about its circumference which act to separate the missile from the tube. Also, the missile includes a plurality of vertical vents arranged about the periphery which also act to reduce resistance.

The guide tube may be provided with a guide tube extension which connects with its upper end for extending the length of the guide tube.

The drop test apparatus includes a centering handle positioned over the upper end of the guide tube which is pivotally mounted at one end and releasably connected at its other end with the upper flange allowing the centering handle to be pivoted providing an entry into the tube through its upper end.

A drop test apparatus for determining the resiliency of playing surfaces which includes a missile for impacting with the surface, a guide for providing substantially unrestricted free flight of the missile to impact, a pair of accelerometers carried by the missiles for producing signals in response to the de-acceleration of the missile upon impact, a converter adapted to receive, convert and send the accelerometer signals and a recording unit recording and displaying the converted signals.

The missile includes a recess in its upper surface which mounts the accelerometers in fixed positions. The recording device is a computer which records and analyzes the signals.

A drop test apparatus for testing the resiliency of playing surfaces comprising a guide for positioning a missile a prescribed distance above a playing surface and for guiding the missile during free fall onto the surfaces. The missile includes a body carrying an accelerometer which is operative to activate upon impact with the surface producing signals in response to the impact. A wireless communicator is provided which is adapted to receive the signals produced by the accelerometer and to convert and transmit these signals to a recording device. The recording device acts to record the signals which indicate the resiliency of the playing surface.

The accelerometer comprises first and second accelerometers. A first of the accelerometer acts to activate the second of the accelerometers upon impact of the missile. The second accelerometer produces the signal sent to and converted by the wireless communicator.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Figure 1A:
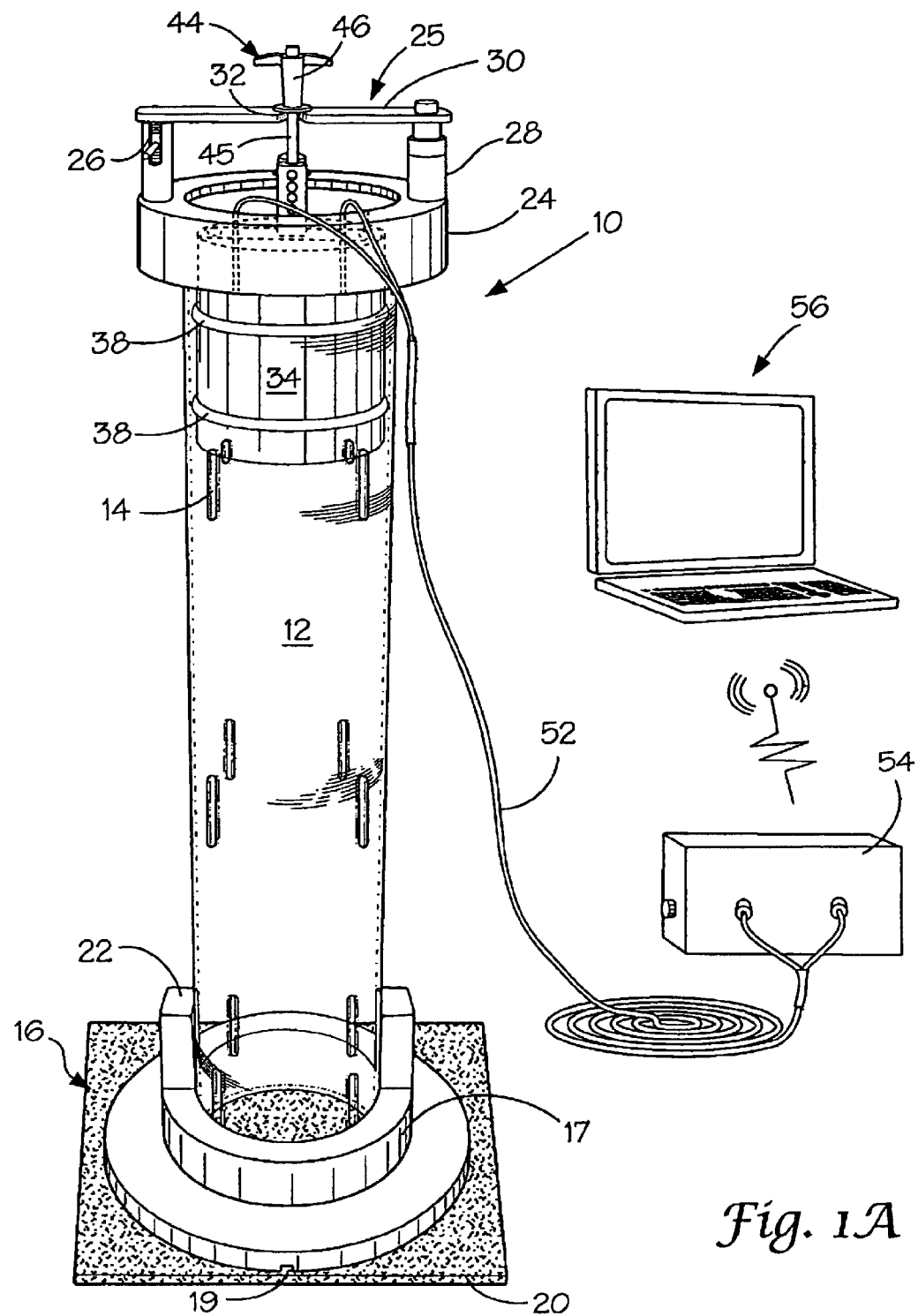
FIG. 1A is a perspective view of the testing apparatus with the missile in the ready position.

Referring now to the drawings, the invention will now be described in more detail.

Figure 1B:
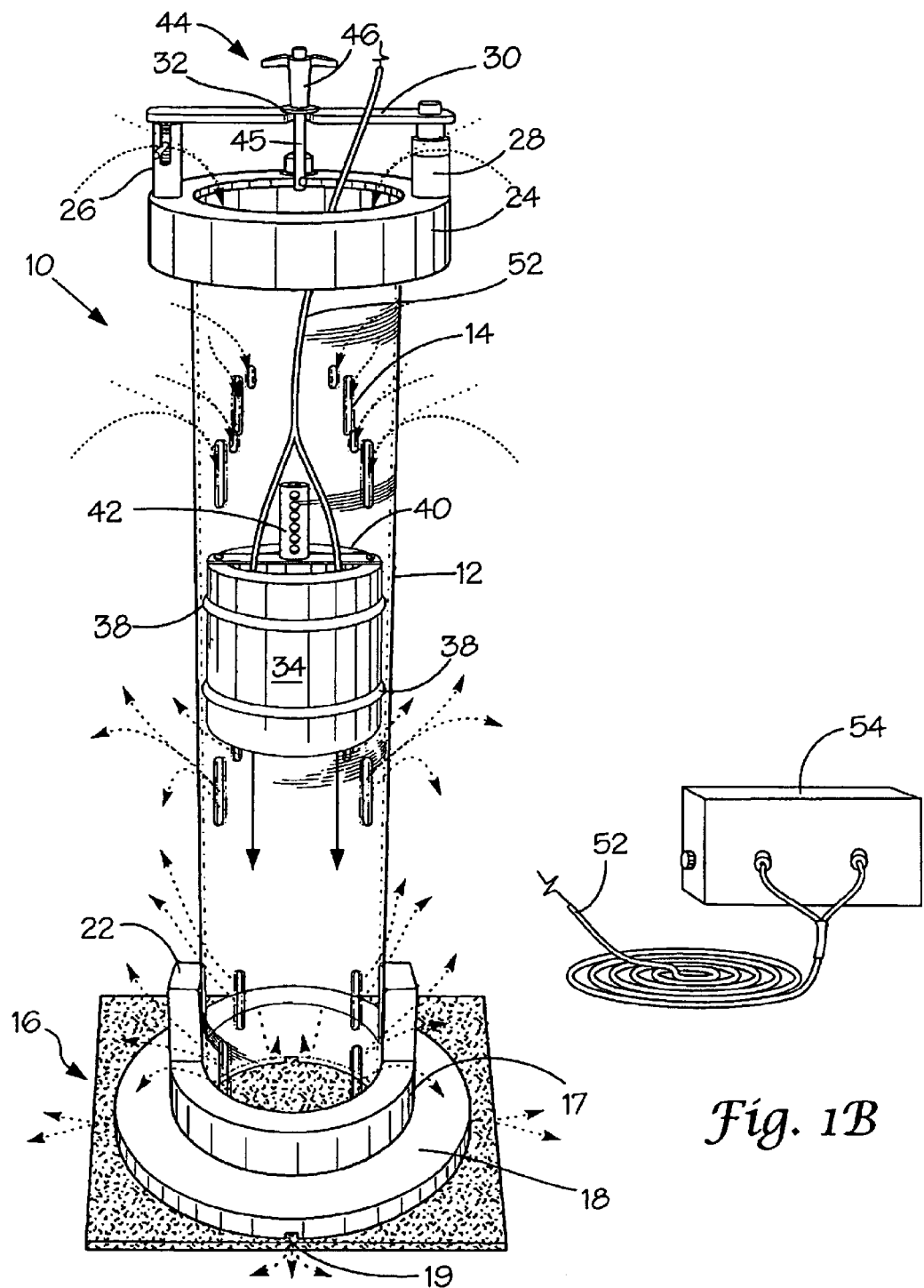
FIG. 1B is similar to FIG. 1A showing the missile in flight.
Figure 1C:
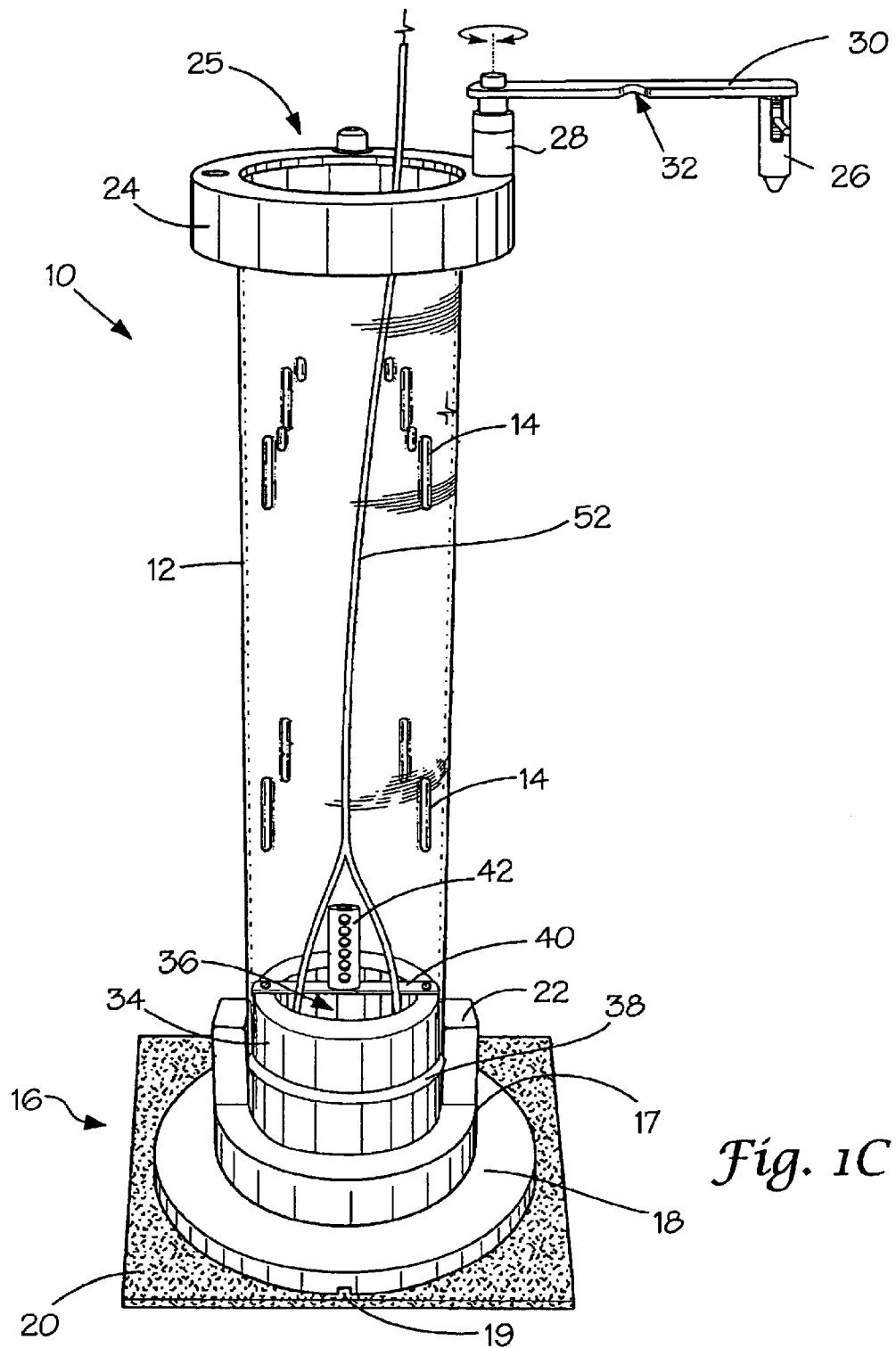
FIG. 1C is similar to FIGS. 1A and 1B showing the missile in the impact position.

Turning now to FIGS. 1A, 1B and 1C, the turf testing apparatus of the invention is illustrated at 10. The arrangement essentially provides a guide for positioning a missile a prescribed distance above a surface and allowing the missile to free fall unrestricted onto the surface. The guide includes drop guide tube 12 which is generally about 30 inches long with a diameter of about 5 7/16 inches. Tube 12 is preferably formed of a clear non-abrasive plastic which allows visibility into the tube and offers minimal resistance to the falling missile, such as an acrylic plastic. The plurality of vertical slits 14 are formed in the tube to extend about its circumference and along its length in a generally harmonic pattern. The slits are to provide exhaust means for the air within the tube during flight of the missile.

The lower end of tube 12 fits into a central opening in base 16. Base 16 is adapted to rest on the surface to be tested and acts to support tube 12 in a generally vertical position. Base 16 includes an extension 17 extending upward from the inner opening. Adjacent the base of extension 17 is a radial flange 18. The lower end of tube 12 fits in the opening and is supported along its axis by extension 17. Flange 18 rests upon playing surface 20 and functions to maintain tube 12 in a generally stationary position.

A plurality of grooves 19 which connect with the opening are formed about flange 18. Grooves 19 act with slits 14 in providing exhaust ports for the air to exhaust during flight of the missile.

A pair of opposed arms 22 are formed on the upper edge of extension 17 which act to further support the tube.

The upper end of tube 12 mounts flange 24 which is formed with a center opening 25 which is slightly smaller than the inner diameter of tube 12. Formed about opening 25 in opposed positions is locking member 26 and an extension 28 which mount centering handle 30 in position over opening 25. Handle 30, at a point aligned with the longitudinal axis, of tube is provided with a notch 32.

Handle 30 is designed to be locked in a drop position over opening 25 by way of locking member 26 as shown in FIGS. 1A and B or rotated about stud 28 into a clear position clear of opening 25 as shown in FIG. 1C. In the locked position notch 32 is aligned with the longitudinal axis of tube 12 and handle 20 is positioned to support missile 34 prior to release. In the clear position, handle 32 is simply positioned away from opening 25 to allow access into tube 12 to retrieve a dropped missile.

Figure 4:
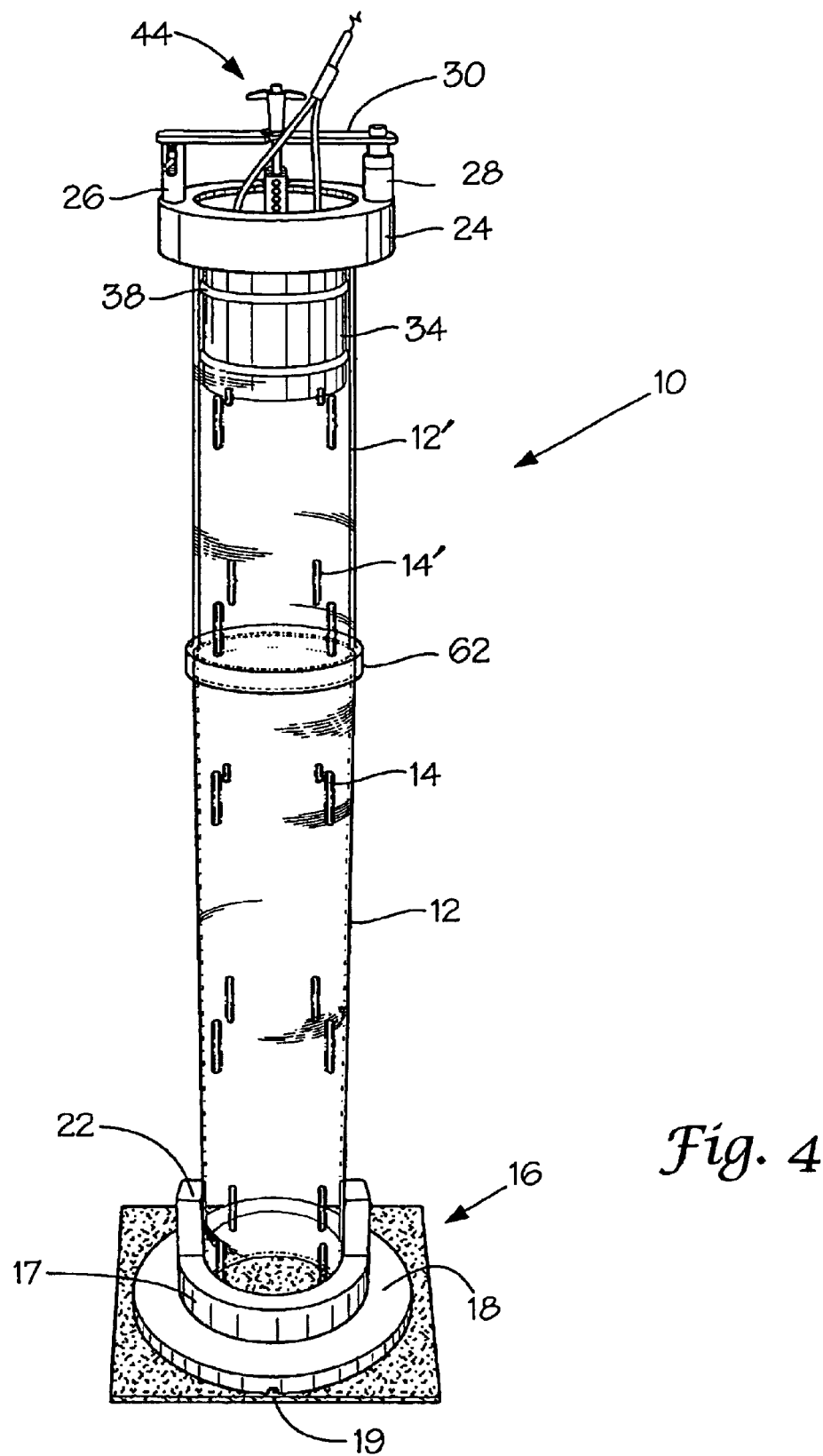
FIG. 4 is a side view of an extension for the guide tube.

In the event that the height provide by tube 12 is insufficient, an extension tube 12' is provided as shown in FIG. 4. Tube 12' is formed to extend the length of tube 12 by 24 inches. Tube 12' includes a flared lower end 62 which is shaped to telescope over the upper end of tube 12. Flange 24 is now positioned over the opposite end of tube 12' in the manner just described.

Figure 2:
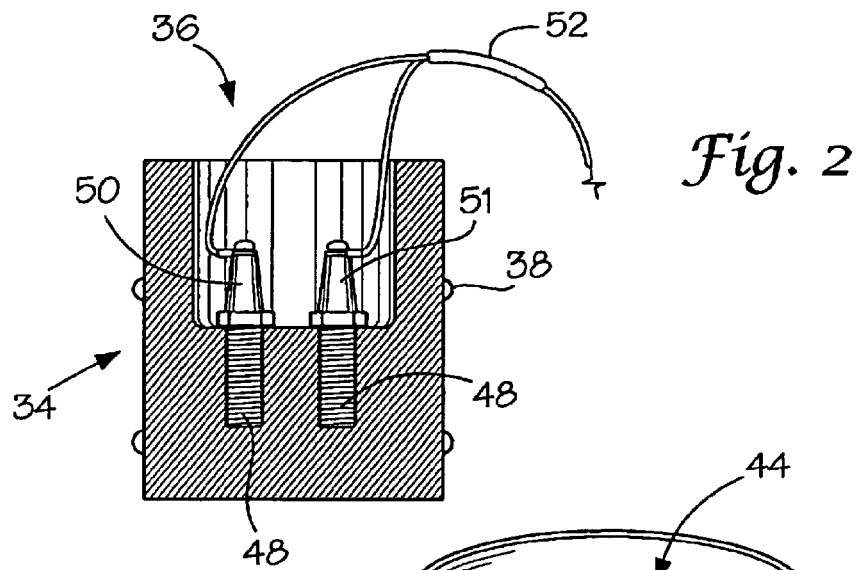
FIG. 2 is a cutaway side view of the missile.
Figure 3:
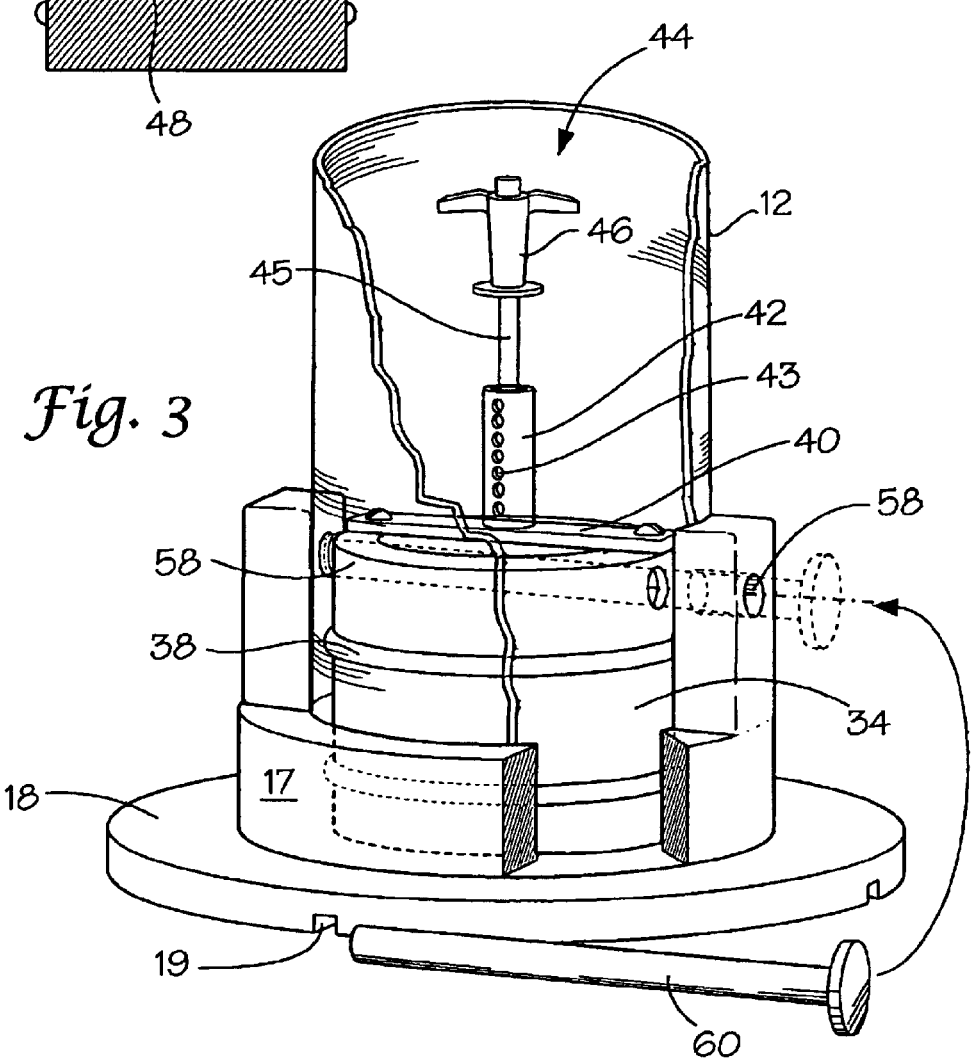
FIG. 3 is an exploded sectional cutaway view showing a locking arrangement for locking the missile for transport. See remarks on FIG. 3.

Turning now to FIGS. 1B, 2 and 3, missile 34 comprises a circular weight, preferably of stainless steel, with a cavity 36 formed in its upper surface. The circumference of missile 34 is slightly less than the inner diameter of tube 12. A pair of bearing rings 38 are located in spaced positions about the periphery of missile 34 and act to provide a substantially friction free engagement with tube 12. Rings 38 may be formed of TEFLON.

It is important that the weight of missile 34 be exact and normally it is formed to that exact weight. Should an abnormality occur the weight may be adjusted by drilling partial holes about the periphery of missile 34.

Bar 40 is secured to the top of the missile and across its vertical axis. An engagement ring 42 is secured with bar 40 also along the vertical axis of missile 34. The engagement ring includes a plurality of engaging holes 43.

A releasable retaining member 44, of known construction, and which includes rod 45 carrying a handle 46 at one end and a gripping member at its opposite end. The handle includes a release button which controls the gripping member. Retaining member 44 is adapted to fit into ring 42 with the engaging member engaging at a selected point with one of the engaging holes 43. Retaining member 44 is connected with handle 30 by way of notch 32 which engages with rod 45 below the lower end of handle 46. Missile 34 is held in position normally to drop 24 inches. By pressing the button on handle 46, the missile is released to fall onto surface 20.

A pair of threaded bores 48 are formed in the base surface of cavity 36. An accelerometer, of a pair of accelerometers 50, 51, is secured in each bore in a stable position. Accelerometer 50 produces a 1 mili-volt signal while accelerometer 51 produces a 100 mili-volt signal. The accelerometers are adapted to measure the acceleration/de-acceleration of the missile on impact with the playing surface.

Each accelerometer 50, 51 is connected to a transmission wire or lead 52 which is connected with wireless communicator 54. Lead 52 is about 6' long allowing ample slack between the missile and the wireless communicator during free fall of the missile.

The wireless communicator is available commercially as 1CHM 20/20 and may be purchased from Oceana Sensor, Inc. The accelerometers are available commercially from PCB Piezotronics, Inc.

Wireless communicator 54 is adapted to receive signals in the form of mili-volts sent by the accelerometers to convert these signals into computer readable information and to relay the converted information to a computer 50 which is equipped and programmed to capture and visually produce data indicating the hardness or resistance of the playing surface. Computer 50 comprises a storage and display unit although other means may be employed to receive the signals from the converter.

In operation the device operates in the following manner. Testing apparatus 10 is set up on a playing surface with base 16 supporting tube 12 in a substantially vertical position. Missile 34 is engaged with handle 46 which is in turn secured in position in notch 32 on bar 40. Communicator 54 is activated. A length of lead 52 is held over the upper end of tube 12 in position to free fall with missile 34 so as to insure no resistance to the fall of missile 34. Missile 34 is designed to fall free of contact with tube 12, however, should slight contact occur during free fall bearing rings 38 are provided to insure that resistance is minimal. The button on handle 46 releases the missile to free flight. Accelerometer 50 is actively producing 1 mili-volt signals during free fall while accelerometer 51 is inactive. The signals from accelerometer 50 are insufficient to be recorded by wireless communicator 54. Upon impact, accelerometer 50 produces a signal sufficient to activate accelerometer 51 which produces 100 mili-volt signals in response to the bounce back or rebound of missile 34 engaging with the playing surface. The signal from accelerometer 51 is received by wireless communicator which converts and sends a computer readable signal to computer 56. The computer generally produces a graft recording the hardness of the playing surface although numerical data may also be displayed.

A locking arrangement is provided for securing the missile in position during transport between testings. As shown in FIG. 3, a bore 58 is provided through arms 22 and missile 34. A pin 60 is provided to pass through arms 22 and missile 34 securing the missile in position in tube 12. Retaining member 44 is preferably secured in ring 42. The arrangement can now easily and safely be placed in a carrying case.

While a preferred embodiment of the invention has been described using specific terms, such description is for illustrative purposes only, and it is to be understood that changes and variations may be made without departing from the spirit or scope of the following claims.

What is claimed is:

1. A drop test apparatus for determining the resiliency of playing surfaces comprising:
    a missile for impacting said surface;
    a guide including a tube and a base for providing substantially unrestricted free flight of said missile prior to impacting said surface;
    said base having radially extending grooves about its lower surface, said grooves acting to vent air from said tube during flight of said missile;
    a pair of accelerometers carried by said missile for producing signals in response to impact of said missile with said surface;
    a converter adapted to receive said accelerometer signals, convert said signals and transmit said converted signals to a storage and display unit; and
    said storage and display unit storing and displaying said converted signals.

2. The drop test apparatus of claim 1, wherein said guide tube comprises a plastic tube having slots along its length and about its periphery so as to provide unrestricted flight for said missile.

3. The drop test apparatus of claim 1, wherein said missile includes a recess in its upper surface, said accelerometers being mounted within said recess.

4. The drop test apparatus of claim 1, wherein said storage and display device is a computer.

5. The drop test apparatus of claim 1, wherein said signals are recorded and displayed in the form of a graph.

6. A drop test apparatus for testing the resiliency of playing surfaces comprising:
    a guide including an elongate tube for positioning a missile a prescribed distance above a playing surface and for guiding said missile during free fall onto said surface;
    said missile having a body having a bearing arranged about its circumference separating said missile from said tube;
    said missile including an accelerometer, said accelerometer being operative to activate upon impact with said surface to produce signals in response to said impact;
    a wireless communicator adapted to receive said signals produced by said accelerometer and to convert and transmit said converted signals to a storage and display device, said storage and display device producing a display in response to said converted signals, whereby;
    resiliency of said playing surface is provided.

7. The drop test apparatus of claim 6 wherein said accelerometer comprises first and second accelerometers, said first accelerometer acting to activate said second accelerometer upon impact of said missile, said second accelerometer producing said signal delivered to and converted by said wireless communicator.

8. The drop test apparatus of claim 6 wherein said accelerometer communicates with said wireless communicator by way of a transmission wire.

9. The drop test apparatus of claim 6 wherein said missile includes a cavity formed in its upper surface, said cavity mounting said accelerometer beneath said upper surface.

10. The drop test apparatus of claim 9 wherein said cavity includes a threaded bore, said accelerometer being mounted in said threaded bore.

11. The drop test apparatus of claim 6, wherein said tube includes a plurality of slits about its periphery for promoting unrestricted free fall.

12. The drop test apparatus of claim 11 including a locking device operative to lock said missile in a stationary position within said tube for transport.

13. The drop test apparatus of claim 11 wherein said tube is formed of synthetic material.

14. The drop test apparatus of claim 11 including a guide tube extension connectable with said second end for extending the length of said guide tube.

15. The drop test apparatus of claim 6 wherein said guide includes a base with radially extending grooves arranged about its lower surface, said grooves acting to vent air from said tube during free flight of said missile through said tube.

16. The drop test apparatus of claim 6 wherein said bearing comprises at least a pair of synthetic rings.

17. The drop test apparatus of claim 6 wherein said missile includes a plurality of vertical vents arranged adjacent its periphery.

18. The drop test apparatus of claim 6 wherein said guide includes a guide tube with open upper and lower ends, a centering handle arranged above said upper end and first means pivotally mounting said centering handle at one end and second means releasably connecting said centering handle at a second end with said guide whereby said centering handle may be pivoted about said first means to allow entry into said guide through said upper end.

* * * * *